(12) United States Patent
Donaldson

(10) Patent No.: US 7,988,288 B2
(45) Date of Patent: Aug. 2, 2011

(54) METHOD FOR VISUAL FIELD TESTING

(75) Inventor: Blair Donaldson, Aberdeen (GB)

(73) Assignee: BID Instruments Ltd., Aberdeen (GB)

( * ) Notice: Subject to any disclaimer, the term of this patent is extended or adjusted under 35 U.S.C. 154(b) by 0 days.

(21) Appl. No.: 12/520,834

(22) PCT Filed: Dec. 21, 2007

(86) PCT No.: PCT/GB2007/005004
§ 371 (c)(1),
(2), (4) Date: Jan. 8, 2010

(87) PCT Pub. No.: WO2008/078106
PCT Pub. Date: Jul. 3, 2008

(65) Prior Publication Data
US 2010/0128222 A1   May 27, 2010

(30) Foreign Application Priority Data

Dec. 22, 2006 (GB) .................................. 0625912.1

(51) Int. Cl.
*A61B 3/14* (2006.01)
*A61B 3/02* (2006.01)
(52) U.S. Cl. ...................... 351/210; 351/237
(58) Field of Classification Search ........... 351/200–246
See application file for complete search history.

(56) References Cited

U.S. PATENT DOCUMENTS

| 4,995,717 | A | * | 2/1991 | Damato | 351/224 |
| 5,737,060 | A | | 4/1998 | Kasha, Jr. | 351/224 |
| 5,946,075 | A | | 8/1999 | Horn | 351/246 |
| 6,367,932 | B1 | * | 4/2002 | Donaldson | 351/237 |
| 6,474,817 | B1 | * | 11/2002 | McKinnon et al. | 351/243 |
| 2004/0057013 | A1 | | 3/2004 | Cappo | 351/224 |
| 2005/0165327 | A1 | | 7/2005 | Thibault | 600/558 |
| 2006/0114414 | A1 | | 6/2006 | McGrath et al. | 351/246 |

FOREIGN PATENT DOCUMENTS

GB   2332271 A   6/1999

* cited by examiner

*Primary Examiner* — Mohammed Hasan
(74) *Attorney, Agent, or Firm* — Stoel Rives LLP; Samuel E. Webb; Yury M. Colton

(57) ABSTRACT

A method of ocular testing is provided using a testing apparatus having a display (2) and a control means (6, 17) for controlling movement of a cursor (7). The method comprises providing a fixation target (T), detecting when an observer (1) moves the cursor (7) over the fixation target, and once the cursor has been moved over, providing a new target on the display (2). The observer (1) is then encouraged to move the cursor (7) over the new target, this then becoming the fixation target. If the observer (1) does not move the cursor (7) over the new target, it is determined that the new target falls outside the observer's visual field. The above is then repeated to build up a visual field of the observer (1) based on the detected and undetected target positions.

21 Claims, 2 Drawing Sheets

▭ Line not seen with 1st test
— Line not seen with 2nd test

METHOD FOR VISUAL FIELD TESTING

This application is the U.S. National Phase of PCT International Application No. PCT/GB2007/005004, filed Dec. 21, 2007, the entirety of which is incorporated herein by reference.

TECHNICAL FIELD

The present invention relates to a method for the measurement of a visual field. In this respect, there are a number of existing tests for measuring and building up a visual field, such as for example the Bjerrum test, the Static Perimetry test and the Optokinetic test.

BACKGROUND

Problems associated with known tests stem from the fact that in each case the observer is required to give some sort of indication or response as to when they see the target in their visual field. The exact point of when the target is seen can be somewhat subjective and unclear and can therefore lead to significant inaccuracies.

More recently, tests have been developed to address the problem of subjectiveness associated with the above tests. Notably, WO 99/226338 describes testing apparatus in which an eye tracker is used to ensure the observer maintains their direction of gaze on a fixation target as other targets are presented on screen. This system offers considerably more accurate visual field results since an observer cannot lose their direction of gaze on the fixation target as new targets are presented. However, this system can suffer from a problem in that the eye tracker used to track a patient's direction of gaze, and the associated processors required to operate the eye tracker, are expensive. Furthermore, eye trackers currently available can suffer from inaccuracies, making operation of the system problematic, particularly if not properly configured.

SUMMARY

An object of the present invention is to seek to overcome the problems associated with such known tests and apparatus.

According to a first aspect of the present invention, there is provided a method of ocular testing using a testing apparatus having a display and means for controlling a cursor on the display, the method comprising the steps of: providing a fixation target on the display at a known target position; detecting when an observer moves the cursor over said fixation target; once the cursor is over the fixation target, providing a new target on the display at a further known target position; detecting if an observer moves the cursor over said new target, the new target then becoming the fixation target; determining that the new target falls outside the observer's visual field if the observer does not move the cursor over the new target; repositioning the new target if it is determined that the new target falls outside the observer's visual field, until it is detected that the observer has been able to move the cursor over the new target, the new target then becoming the fixation target; recording the detected and undetected target positions; and repeating the steps of providing a new target on the display a number of times to build up a visual field of the observer based on the detected and undetected target positions.

With such a method, the fixation target is a target over which the observer is initially encouraged to move the cursor. The new target is a visual field target provided somewhere on the screen in what would be the visual field of a normal observer. If the observer is aware of the visual field target while looking at the fixation target, then be is encouraged to move the cursor over it. The visual field target then becomes the fixation target at a revised known target position. A new visual field target can then be provided on the display and the process is repeated to build up a visual field.

With such a method, the test can be implemented with relatively cheap apparatus and without the need for an expensive eye tracking means.

With certain observers, a substantial part of the visual field on one side may be missing such that as successive targets are presented, only those not in the missing part are seen. This could have an effect in gradually moving the fixation target further and further to one side of the display. Consequently, the useful area of the screen for presenting further targets will be diminished. To counter this the method may further comprise means for repositioning the fixation target whilst viewed by the observer to create additional space on the screen for displaying the new target.

Conveniently, a new target not seen by the observer is repositioned after a predetermined time interval.

Preferably, a new target not seen by the observer is moved in incremental steps. In this respect, this gives the observer an opportunity to establish whether such a target is in their visual field. If the observer is not aware of such a target then it is repositioned, for example closer to the fixation target, to try to establish the limits of the observer's visual field at that orientation.

The repositioning of the fixation target is preferably carried out with the fixation target in constant view of the observer. In this manner, the effect of the repositioning of the fixation target on the data on the visual field of the observer is readily reconciled.

Conveniently, the targets are moved under the control of a computer.

Conveniently, the means for controlling the cursor is an electronic pen and pad arrangement or a mouse. These have proven to afford the most reliable means for use by a wide cross-section of observers, including the elderly.

Conveniently, the cursor is a circle being moveable for surrounding the fixation target. Alternative arrangements are possible including a cross hair arrangement.

Preferably, the size, shape and/or position of the fixation target is configured to change for engaging the observer. This may mean the fixation target oscillates, vibrates, expands/contracts, moves from side to side or changes in contrast or colour. In this way, the observer's attention is more likely to be maintained on the fixation target.

Conveniently, the fixation target is arranged to move and the observer is encouraged to maintain the cursor over the fixation target; and wherein the new target is only displayed when the cursor is over the fixation target or being moved directly towards the new target; and wherein the new target is moved with said fixation target to maintain it at a constant position relative to the fixation target until the cursor is moved over the new target. Having the fixation target move ensures that the observer has to maintain their attention thereon.

Conveniently, the fixation moves in a random pattern.

Alternatively, the fixation moves in a regular pattern. This has been found to be more successful when testing elderly patients.

Conveniently, the method further comprises the step of repositioning the fixation target whilst the observer maintains the cursor over the fixation target for creating additional space on the display for displaying the new target or a subsequent new target.

Conveniently, the step of repositioning the new target falling outside the observer's visual field is performed after a predetermined time interval.

Preferably, the step of repositioning of the new target comprises moving the new target in incremental steps.

Conveniently, the method further comprises the steps of providing a blind spot target in a position relative to said fixation target which is known to be in the observer's blind spot; determining that the observer has lost fixation on said fixation target if they move the cursor over said blind spot target; instructing the observer to return the cursor to the fixation target when it is determined they have lost fixation; and removing said blind target when the observer moves the cursor over said fixation target. This method step is used to test whether the observer is carrying out the test correctly, and is included early on in the whole test cycle. If the observer moves the cursor over the blind spot target, it is clear that the observer is not carrying out the test correctly.

Conveniently, the method further comprises conducting a pre-test calibration procedure, said pre-test calibration procedure comprising the steps of: providing a pre-test fixation target on the display at a known target position; detecting when an observer moves the cursor over said pre-test fixation target and encouraging the observer to continue to look at the pre-test fixation target; once the cursor is over the pre-test fixation target, providing a contrast target on the display at a different position to said pre-test fixation target, said contrast target having a low contrast relative to the background of the display; encouraging the observer to move the cursor over said contrast target to identify the contrast target; increasing the contrast of said contrast target relative to said background until the observer has identified the contrast target; recording the contrast level at which the observer identifies the contrast target; and repeating the above steps until a threshold for recognition of the contrast target relative to the background is determined.

Conveniently, the step of recording the minimum contrast level at which the observer identifies the contrast target (this level being the threshold level) further comprises the step of recording the time taken for an observer to identify a suprathreshold target and using that data to determine the observer's reaction time.

Conveniently, the method further comprising conducting a pre-test calibration procedure, said pre-test calibration procedure comprising the steps of: providing a pre-test fixation target on the display at a known target position; detecting when an observer moves the cursor over said pre-test fixation target; once the cursor is over the pre-test fixation target, providing a new target on the display at a further target position; detecting if the observer moves the cursor over said new target and how long it takes for the observer to move the cursor over said new target from when it is displayed, the new target then becoming the pre-test fixation target; repeating the above steps to calibrate the observer's speed of response.

Conveniently, the method incorporates the step of detecting whether or not the observer is not keeping their gaze on the fixation target using a gaze detection means. Conveniently, the method may pause the test if the gaze detection means detects that the observer is not keeping their gaze on the fixation target. This may in certain embodiments be accomplished using simple gaze detection apparatus whilst displaying the visual field target at extreme or wide positions on the display. The gaze detection means may comprise a video camera and suitable software for the computer. For example, a gaze position can be recorded when a cursor moves over a new target, and if the software detects a change in the recorded gaze position, it pauses the test until the video image again corresponds to the recorded gaze position.

The results from the method may be recorded in graphical or pictorial form, representing the visual field of the observer. The results from testing the same observer at different times or different target contrast levels may further be superimposable for indicating the deterioration/progress of the observer, as well as the severity of their defect of visual field.

Preferably, information relating to the test is provided on a single screen, suitably screened off between an observer and an Examiner. Alternatively, the information is displayed on separate screens.

BRIEF DESCRIPTION OF THE DRAWINGS

Examples of the present invention will now be described with reference to the accompanying drawings of which:—

DETAIL DESCRIPTION

Figure 1:
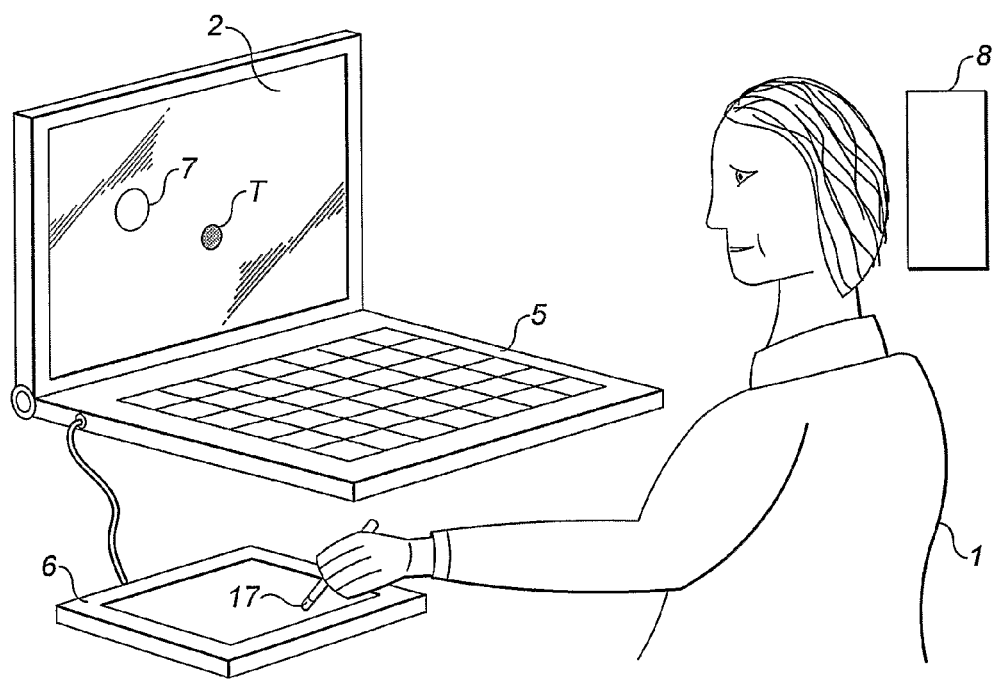
FIG. 1 shows diagrammatically apparatus for use in the present invention.

FIG. 1 shows the testing apparatus for use in the present invention. As shown, an observer 1 is positioned to view a display 2 showing a target T. In the present case, the targets is displayed on a screen, such as an LCD screen. Clearly however, the display could take the form of any suitable means for displaying targets to an observer. For example, the display could involve the use of alternative visual display units (VDU), such as CRT, or a screen onto which targets are projected.

A computer processing unit 5 is used to control the presentation of targets T on the display 2, as well as record their detection. An electronic/digital pen 17 and pad/pallet 6 arrangement is connected to the computer 5 and is used to control the movement of cursor 7 on the display 2. Alternative control means could also be used such as, for example, a mouse or a joystick.

A headrest 8, provided at a known distance from the screen may be used to maintain a constant distance between the observer and the screen.

In one embodiment (not shown), around 90% of the screen may be shown to the observer with the remainder, such as a strip across the top of the screen, being hidden from the observer but visible to an Examiner, the strip showing details of the test being carried out and options for running the test. These options can only be accessed by the Examiner using separate controls. The information for the observer and Examiner may be provided on the same screen, suitably screened off, or may be provided to two separate screens.

In this illustrated embodiment of the invention, the cursor 7 is provided in the shape of a circle or ring, which can be moved over a target T displayed on the display 2 to encircle it.

Prior to the main visual field test, a pre-test calibration is performed in order to assess an observer's responses and calibrate the testing system for that observer subsequent operations.

The pre-test involves presenting a succession of targets onto the display and detecting the speed at which the observer responds, and the contrast threshold at which the observer identifies a target. At the start of the pre-test, after an initial explanation and description provided to the observer, a first contrast target is presented on the display. Initially, this contrast target has a low contrast relative to the background of the display, having effectively the same brightness as the background screen. As the test continues, the contrast level of the contrast target is increased. An observer is encouraged to move the cursor 7 over the contrast target as soon as they become aware of this target. At certain level, the observer becomes aware of the target and will move the cursor 7 over it. Data representing the contrast level at which this occurs and the speed at which an observer can move the cursor over the target is recorded. This cycle is repeated until a sufficient number of results are recorded to determine a reliable average contrast threshold for recognition value and an averaged reaction time value. These values can then be used during subsequent tests.

An example of the main test will now be described with reference to FIGS. 2 and 3.

Figure 2:
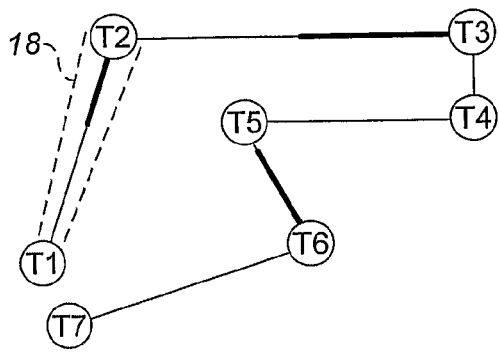
FIGS. 2 and 3 show schematically apparatus for use with the present invention.
Figure 3:
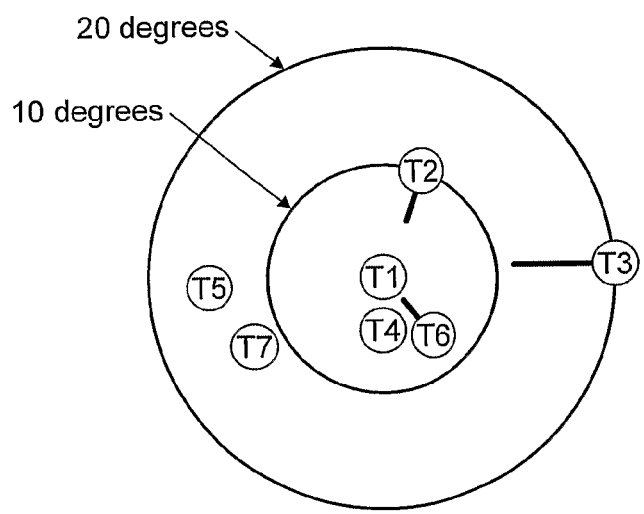

FIG. 2 schematically shows a target T1 at the starting point of a visual field test. On displaying this target, an observer is encouraged to move the cursor 7, under the control of pen/pallet 6, over the target. The target T1 thereby becomes a fixation target. Establishing the cursor over the target can be confirmed by a sound or change in the displayed information.

Once it is confirmed that the observer has moved the cursor over this target, target T2 is then provided on the screen as a visual field target. The observer is encouraged to move the cursor over target T2 if he becomes aware of this target while still looking at target T1. Once the cursor has been moved over target T2, it then becomes the new fixation target. At this point target T1 disappears and a new target, target T3 appears and the process continues for targets T4 to T7.

The above system works on the basis that in order for an observer to move their cursor over the target, they need to be gazing at it. Once an observer has moved the cursor over the target, a new visual field target is displayed, prompting the observer to then move the cursor to the new target to select it.

In this connection, by employing the reaction speed and threshold values determined during the pre-test calibration described above, the time at which the new target is selected can thereby be used to assess if the new target is in the observer's visual field when focussing on the fixation target. That is, if an observer moves the cursor to the new target relatively quickly, based on the pre-test results, it is determined that the new target was in their visual field. However, if the observer does not move to the new target, then it is determined that the new target was not in their visual field.

To help to maintain the observer's direction of gaze, the fixation target may be configured to vibrate or oscillate or otherwise change its appearance, once it has been selected by the cursor. This oscillation or movement helps to maintain the observer's direction of gaze on the target as their eyes are drawn to the movement.

In an alternative embodiment, each fixation target is moved throughout the test and the observer is encouraged to continue to track the fixation target with the cursor 7. As the fixation target is moving, the observer must continue to gaze at the target in order to keep the cursor over it. When new visual field targets are displayed, they are moved in the same pattern as the fixation target in order to remain in a fixed position relative to the fixation target.

As with the previous embodiment, an observer moves from target to target as they appear on the display. However, in this embodiment, movement of the fixation target ensures the observer maintains gaze on this target as other targets are displayed.

In the event the cursor moves off the current fixation target, the test is paused until they return the cursor. However, in order to allow the cursor to be moved to the next visual field target, a movement corridor or channel is effectively formed between the targets. This is represented by dashed line 18 shown in FIG. 2. Accordingly, during the test, an observer is able to move directly to new targets, but any other movement off the current fixation target results in the test being paused.

In order to detect a loss of fixation from the requested direction of gaze at the fixation target, the test further comprises the steps of providing a blind spot target in a position relative to said fixation target which is known to be in the observer's blind spot. This should not produce any response from the patient. In other words if the observer moves the cursor over said blind target, then they have lost fixation on said fixation target. In this event, the observer is instructed to return the cursor to the fixation target and said blind target is removed. This method step is included early on in the whole test cycle and is repeated several times during the test to ensure correct requested fixation.

In either of the above embodiments, if a new/visual field target is not seen, it can be moved under computer control to where it is seen and the position recorded, or other targets are displayed one at a time until one is seen and the process continues further. By varying the distance and angle direction of the new visual field target in relation to the fixation target, which was the previous visual field target, a visual field can be built up. Hence, the observer simply follows targets appearing on the screen with the cursor.

The apparatus may further comprise means for repositioning the display position of the fixation target to allow a new target to be positioned on the screen. In this respect, with certain observers, a substantial part of the field on one side may be missing such that as successive targets are presented, only those not in the missing part are seen. This could have an effect in gradually moving the fixation target further and further to one side of the display. Consequently, the useful area of the screen for presenting further targets will be diminished. To counter this, the fixation target can be moved under the control of the computer to a position where there is sufficient space left on the display to present further targets and thus continue the test. Such a means for repositioning the target may for example be provided in the form of software for the computer.

As mentioned above, in a preferred embodiment of the present intention a pre-test is conducted in order to assess an observer's reactions to the presentation of targets. This can be used to establish a baseline or benchmark by which subsequent measurements during the main test can be assessed.

It will be appreciated that the present invention may be applied to many different configurations, the detailed embodiments being straightforward for those skilled in the art to implement.

For example, in the above described embodiment, an electronic pen/pallet 6 is used as the means to control the cursor 8, although other means could alternatively be used such as a joystick, mouse, roller ball or touch-screen. Similarly, a circular cursor has been described above, although different cursors could alternatively be used, such as a cross hair.

A relatively simple gaze detection means may be employed to detect whether or not the observer is keeping their gaze on the fixation target. In this regard, at an early part of the testing cycle, a new target may be displayed at a wide extremity of the display, and the gaze detection means be activated to detect whether or not the observer's gaze is obviously orientated in an appropriate direction. For such a purpose a relatively simple gaze detection means may be employed. Such a simple gaze detection means can pause the test if it detects that the direction of gaze moves away from the fixation target except in the direction of the new target. The eye movement is not tracked to the new target but if it is clear the eye moves in another direction the test is paused.

FIG. 2 refers to the observer's screen presentation of the sequence of 7 targets. The thick black lines refer to the positions where T2, T3 and T6 were not seen.

Figure 4:
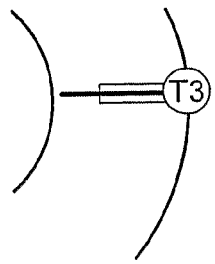
FIG. 4 shows two test results from the same eye for one target from different times.

FIG. 4 shows the superimposition of two tests of T3, the first test is represented by a white line, the second by a black line. This shows that the unseen positions of T3 have increased in the second test. Colours can be used in place of black and white, for example green for the first test and red for the second test. If the second test is worse than the first, the end of the line nearest the centre will show red, and if it had been better it would have been be green.

The invention claimed is:

1. A method of ocular testing using a testing apparatus having a display and observer controllable means for controlling movement of a cursor on the display, the method comprising the steps of:
    providing a fixation target on the display at a known target position;
    detecting when an observer moves the cursor over said fixation target;
    once the cursor is over the fixation target, providing a new target on the display at a further known target position;
    detecting if an observer moves the cursor over said new target, the new target then becoming the fixation target;
    determining that the new target falls outside the observer's visual field if the observer does not move the cursor over the new target;
    repositioning the new target if it is determined that the new target falls outside the observer's visual field, until it is detected that the observer has been able to move the cursor over the new target, the new target then becoming the fixation target;
    recording the detected and undetected target positions;
    and repeating the steps of providing a new target on the display a number of times to build up a visual field of the observer based on the detected and undetected target positions.

2. A method according to claim 1, wherein a new target not seen by the observer is repositioned after a predetermined time interval.

3. A method according to claim 1, wherein a new target not seen by the observer is moved in incremental steps.

4. A method according to claim 1, wherein the means for controlling the cursor is an electronic pen and pad arrangement or a mouse.

5. A method according to claim 1, wherein the cursor is a circle moveable for surrounding the fixation target.

6. A method according to claim 1, wherein the size, shape and/or position of the fixation target is configured to change for engaging the observer.

7. A method according to claim 1, wherein the fixation target is arranged to move and the observer is encouraged to track said movement by maintaining the cursor over the fixation target;
    and wherein the new target is only displayed when the cursor is over the fixation target or being moved directly towards the new target;
    and wherein the new target moves with said fixation target to maintain it at a constant position relative to the fixation target until the cursor is moved over the new target.

8. A method according to claim 7, wherein the fixation target moves in a random pattern.

9. A method according to claim 7, wherein the fixation target moves in a regular pattern.

10. A method according to claim 1, further comprising the step of repositioning the fixation target whilst the observer maintains the cursor over the fixation target for creating additional space on the display for displaying the new target or a subsequent new target.

11. A method according to claim 10, wherein the step of repositioning the new target falling outside the observer's visual field is performed after a predetermined time interval.

12. A method according to claim 1, the method further comprising the steps of providing a blind spot target in a position relative to said fixation target which is known to be in the observer's blind spot;
    determining that the observer has lost fixation on said fixation target if they move the cursor over said blind target;
    instructing the observer to return the cursor to the fixation target when it is determined they have lost fixation;
    and removing said blind target when the observer moves the cursor over said fixation target.

13. A method according to claim 1, the method further comprising conducting a pre-test calibration procedure, said pre-test calibration procedure comprising the steps of:
    providing a pre-test fixation target on the display at a known target position;
    detecting when an observer moves the cursor over said pre-test fixation target and encouraging the observer to continue to look at the pre-test fixation target;
    once the cursor is over the pre-test fixation target, providing a contrast target on the display at a different position to said pre-test fixation target, said contrast target having a low contrast relative to the background of the display;
    encouraging the observer to move the cursor over said contrast target to identify the contrast target;
    increasing the contrast of said contrast target relative to said background until the observer identified the contrast target;
    recording the contrast level at which the observer identifies the contrast target; and repeating the above steps until a threshold for recognition of the contrast target relative to the background is determined.

14. A method according to claim 13, the step of recording the contrast level at which the observer identifies the contrast target further comprises the step of recording the time taken for an observer to identify a supra-threshold target and using that data to determine the observer's reaction time.

15. A method according to claim 1, the method further comprising conducting a pre-test calibration procedure, said pre-test calibration procedure comprising the steps of:
    providing a pre-test fixation target on the display at a known target position;
    detecting when an observer moves the cursor over said pre-test fixation target;
    once the cursor is over the pretest fixation target, providing a new target on the display at a further target position;
    detecting if the observer moves the cursor over said new target and how long it takes for the observer to move the cursor over said new target from when it is displayed, the new target then becoming the pre-test fixation target;
    repeating the above steps to calibrate the observer's speed of response.

16. A method according to claim 1, wherein the method incorporates the step of detecting whether or not the observer is keeping their gaze on the fixation target using a gaze detection means.

17. A method according to claim 16, further comprising the step of pausing the test if the gaze detection means detects that the observer is not keeping their gaze on the fixation target.

18. A method according to claim 16, wherein the gaze detection means comprises a video camera and suitable software.

19. A method according to claim 1, wherein results from the method are recorded in graphical or pictorial form, representing the visual field of the observer.

20. A method according to claim 19, wherein the results from testing the same observer at different times or different target contrast levels are superimposable.

21. A method according to claim 1, wherein information relating to the test is provided on a single screen, suitably screened off between an observer and an Examiner.

* * * * *